US010539550B2

(12) United States Patent
Gerde

(10) Patent No.: US 10,539,550 B2
(45) Date of Patent: Jan. 21, 2020

(54) EXPOSURE SYSTEM

(71) Applicant: INHALATION SCIENCES SWEDEN AB, Huddinge (SE)

(72) Inventor: Per Gerde, Trosa (SE)

(73) Assignee: INHALATION SCIENCES AB, Huddinge (CH)

( * ) Notice: Subject to any disclaimer, the term of this patent is extended or adjusted under 35 U.S.C. 154(b) by 1343 days.

(21) Appl. No.: 14/662,363

(22) Filed: Mar. 19, 2015

(65) Prior Publication Data

US 2015/0192566 A1 Jul. 9, 2015

Related U.S. Application Data

(63) Continuation of application No. PCT/SE2013/051111, filed on Sep. 25, 2013.

(60) Provisional application No. 61/705,418, filed on Sep. 25, 2012.

(51) Int. Cl.
*G01N 33/50* (2006.01)
*G01N 15/06* (2006.01)

(52) U.S. Cl.
CPC ..... *G01N 33/5026* (2013.01); *G01N 33/5044* (2013.01); *G01N 2500/04* (2013.01)

(58) Field of Classification Search
None
See application file for complete search history.

(56) References Cited

U.S. PATENT DOCUMENTS

| 4,429,835 A * | 2/1984 | Brugger ............... A61M 11/06 128/200.18 |
| 5,596,982 A * | 1/1997 | Blaha-Schnabel ......................... A61M 15/0086 128/200.14 |
| 5,755,965 A * | 5/1998 | Reiber ............... B01D 19/0057 210/512.1 |
| 6,003,512 A * | 12/1999 | Gerde ................... A61M 15/00 128/203.15 |
| 6,042,628 A * | 3/2000 | Nishikiori ............. B01D 45/16 55/337 |

(Continued)

FOREIGN PATENT DOCUMENTS

| WO | 03089036 A1 | 10/2003 |
| WO | 2009002267 | 12/2008 |

(Continued)

OTHER PUBLICATIONS

Riley T, Jones A, Bogalo Huescar M, Roche T: In Vitro Method for Determining the Dissolution Rate of Inhalation Aerosols. Respiratory Drug Delivery. 2008; 2:541-544; figure 1; Methods.

(Continued)

*Primary Examiner* — Eddy Saint-Vil
*Assistant Examiner* — William D Ermlick
(74) *Attorney, Agent, or Firm* — Gabriela B. Tomescu, Esq.; Bergenstråhle & Partners AB

(57) ABSTRACT

The invention relates to methodologies of obtaining a controlled exposure of an aerosol to a model material. The invention also provides an exposure cap and a system for studying or predicting the interaction between a model material, e.g. a cell, and an aerosolized agent. The controlled exposure of the aerosol to the model material, makes is possible to accurately calculate the mass-balance of the aerosol exposure.

8 Claims, 4 Drawing Sheets

(56) References Cited

U.S. PATENT DOCUMENTS

| | | | | |
|---|---|---|---|---|
| 6,103,534 A * | 8/2000 | Stenger | G01N 21/76 | 422/52 |
| 6,210,575 B1 * | 4/2001 | Chase | B01D 29/118 | 209/12.1 |
| 8,176,766 B1 * | 5/2012 | Ruiz | G01N 33/497 | 422/84 |
| 9,909,956 B1 * | 3/2018 | St Amant, III | G01N 1/2211 | |
| 2003/0172632 A1 * | 9/2003 | Matsubara | B01D 45/16 | 55/417 |
| 2003/0196654 A1 * | 10/2003 | Stein | A61M 15/0086 | 128/200.23 |
| 2005/0279349 A1 * | 12/2005 | Patton | A61M 15/0086 | 128/200.14 |
| 2008/0092734 A1 * | 4/2008 | Benner | B01D 45/16 | 95/26 |
| 2009/0158932 A1 * | 6/2009 | Arnold | A47L 9/1608 | 95/271 |
| 2009/0288560 A1 * | 11/2009 | Ruppel | F01M 13/04 | 96/408 |
| 2010/0196866 A1 * | 8/2010 | Gerde | G09B 23/12 | 434/272 |
| 2010/0212667 A1 * | 8/2010 | Smith | A61K 9/0075 | 128/203.15 |
| 2010/0297635 A1 * | 11/2010 | Olin | A61B 5/411 | 435/6.11 |
| 2011/0011158 A1 * | 1/2011 | Bodily | G01N 1/2211 | 73/23.41 |
| 2011/0011160 A1 * | 1/2011 | Gerde | A61B 5/0813 | 73/28.01 |
| 2011/0111387 A1 * | 5/2011 | Wu | G01N 1/2202 | 435/5 |
| 2011/0308311 A1 * | 12/2011 | Dalla Betta | G01F 1/6842 | 73/170.12 |
| 2012/0000366 A1 * | 1/2012 | Nixdorff | B01D 45/12 | 96/239 |
| 2012/0168634 A1 | 7/2012 | Egen et al. | | |
| 2013/0217029 A1 * | 8/2013 | Sislian | A61B 5/082 | 435/6.15 |
| 2014/0116256 A1 * | 5/2014 | Yamasaki | B01D 45/16 | 96/414 |
| 2015/0150803 A1 * | 6/2015 | Boucher | A61M 11/06 | 128/200.16 |
| 2015/0297118 A1 * | 10/2015 | Londahl | A61B 5/08 | 600/532 |
| 2016/0090881 A1 * | 3/2016 | Copley | B01D 45/08 | 55/332 |
| 2016/0202222 A1 * | 7/2016 | Roberts | G01N 1/2202 | 435/5 |
| 2017/0299477 A1 * | 10/2017 | Milton | G01N 1/2208 | |
| 2017/0299561 A1 * | 10/2017 | Roberts | G01N 1/2202 | |
| 2018/0200726 A1 * | 7/2018 | Clavaguera | G01N 15/0266 | |

FOREIGN PATENT DOCUMENTS

| | | |
|---|---|---|
| WO | WO 2008153493 | 12/2008 |
| WO | WO-2009002267 A1 * 12/2008 | ........... A61B 5/0813 |
| WO | WO 2012154834 | 11/2012 |
| WO | WO2013085909 | 6/2013 |

OTHER PUBLICATIONS

Li D, Zhuo W, Yi Y, Chen B, Liu H: A new sampler for simulating aerosol deposition in the respiratory tract. Nuclear Science and Techniques. 2008; 19(3): 169-173; figure 4; 3.3 Configuration of the sampler.

* cited by examiner

EXPOSURE SYSTEM

This application is a continuation of PCT Application No. PCT/SE2013/05111, filed Sep. 25, 2013, which claims benefit to U.S. Provisional Application No. 61/705,418, filed Sep. 25, 2012, the entire contents of each of which are hereby incorporated by reference.

FIELD OF THE INVENTION

The present invention relates to a method and a system for studying the controlled interaction of a model material and an aerosol.

BACKGROUND OF THE INVENTION

There is a strong driving force to develop new reliable in vitro tests to reduce the number of animal tests both in the environmental research area as well as in the drug industry. There are a number of in vitro systems developed for simulating toxic or therapeutic exposures using cultured cell systems. Some systems are developed for simulating skin, while other systems are developed to simulate the gastrointestinal canal and the respiratory tract. The respiratory tract is perhaps the most complicated to simulate, since the cultured airway epithelial cells should be exposed directly from the air with only a thin layer of liquid covering the cell surface; a so called air lifted condition. This is a particular problem if the cells shall be exposed to airborne particles. One postulation for repetitive exposure is a deagglomerated particle aerosol generated in small volumes, which is provided with the technology according to the U.S. Pat. No. 6,003,512 developed by Inhalation Sciences Sweden AB (ISAB). ISAB has also developed a spray-drying technique (WO 2004/041900) which can quickly reformulate small portions of substance to a fine powder in high yield, to be used in the dustgun machine. The dust gun aerosol generator has showed to be a useful tool to combine with an isolated, ventilated, and perfused lung of rodents (IPL) as is disclosed in P. Gerde et al. Inhalation Toxicology, 2004, 16, 45-52, wherein the pulmonary deposition of diesel soot was studied. During inhalation exposures with drug candidates, deposition of a studied substance in the target region of the lungs is a desired process that is always accompanied by unwanted losses of study material through deposition in delivery equipment and in non-target regions of the respiratory tract. Early in the development process of drugs intended for inhalation delivery, substance loss is a critical factor preventing often decisive early tests via inhalation. Two major mechanisms lead to wall deposition of particles when an aerosol is flowing through a duct: aerodynamic losses and electrostatic losses. Aerodynamic losses are contributed by diffusion, sedimentation, impaction, and interception of particles and are influenced primarily by the mass median aerodynamic diameter (MMAD) of the studied aerosol and by the fluid dynamics of the duct system under study. Aerodynamic losses can be reasonably well predicted with theoretical models. Electrostatic losses are superimposed on the aerodynamic losses, and depend strongly on material properties of the studied powder and the walls of the duct system. Electrostatic losses are more erratic and difficult to predict, and can be the dominating deposition mechanism of a studied aerosol. This unpredictable behavior of powder aerosols leads to substance losses not only to vessel walls of aerosol generator equipment, exposure systems, and to non-target regions of the respiratory tract, but also during the adjustment of exposure parameters needed to attain target exposures in study subjects. It is the intent of the current invention to address these problems. Electrostatic methods have also been devised to improve aerosol deposition in cell culture. However, these methods are more suitable for very dilute aerosols of nano-sized particles, often of air pollution origin, and are not suitable for denser pharmaceutical aerosols of clinical relevance.

There are several available methods for studying cultured airway cells are e.g. special culture wells developed to grow lung cells on top of a permeable membrane and a reservoir of perfusate under the membrane to create close contact between the airway epithelium and the surrounding air, similar to the in vivo situation. Corning has developed the "Transwell system", where confluent and even ciliated epithelial cells may be cultured and used in experiments. There are similar systems available from Becton, Dickinson and Company; Falcon™. The company Epithelix provides ready to use, fully differentiated epithelial cells with cilia function cultured in Transwell wells, i.e., MucilAir, but they do not have a method for carrying out controlled exposures of such cells to respirable aerosols. The company Vitrocell provides cultivation- and exposure system that consists of a cell culture module based on the Transwell system and proprietary aerosol exposure units. This system accomplishes deposition of particles on a surface by the perpendicular impaction of an aerosol-laden stream onto the study surface. However, the main drawbacks with the methods available today are; lack of suitable method to create a homogenous aerosol with sufficient concentration and correct particle size distribution of the compound to be tested, and finally; poor dose control. There is certainly a need for improvement of in vitro based methods in this field. Such improvements can be accomplished by providing a well controlled method suitable for screening cell cultures for influence by all kinds of airborne particles; e.g. toxicity tests, drugs, diagnostics, metabolic studies, where also influence on the development- or differentiation or gene regulation can be studied (gene regulation studies) etc.

The invention as described in following sections obviates at least some of the disadvantages in this technology and provides a screening model that makes it possible to better study the controlled exposure of an aerosol on a model material resembling the air-blood-barrier in the respiratory tract, in vitro.

DESCRIPTION OF THE INVENTION

The present invention generally provides an improved model system for controlled aerosol exposures, which can be based on a model material that resemble the natural air-blood-barrier of the airways in order to support the prediction of how candidate substances for subsequent drug development deposit, absorb and metabolize following administration to the respiratory tract.

The improved system supports a reliable determination of a mass balance and the deposited dose of an aerosolized test substance, while minimizing losses of the dispensed dose of aerosolized drug in the equipment outside the exposure subject (model material) and allowing for recovery of equipment-deposited material after the exposure series. It is also of importance that the exposure of the aerosolized drug to the surface model material can be admitted to resemble the process in the lung following an inhaled dose of a drug.

For this purpose the systems of the present invention include an aerosol transporting arrangement from an aerosol generator and an exposure unit. The exposure unit includes an exposure cap, a container comprising the model material and a perfusion tray. These parts and their improvements will be described in the following sections.

In the present context, the "air-blood-barrier" means the interface between the air and the tissue of the respiratory tract. Typically, the mucosal tissue of the conducting airways and the alveolar tissue of a lung are examples of air-blood-barriers.

The term "aerosol" is frequently referred to as a mist of liquid droplets; however term as used in the present context refers to a suspension of solid particles in an air flow. Accordingly the term "aerosol" can also mean an "aerosol bolus" describing a volume of air with suspended particles of a formulation. The terms "aerosol," "particles," "aerosol particles," "aerosolized formulation" and similar are used interchangeably in the present context and will refer to particles of formulation comprised of pharmaceutically active drug and carrier which are formed for aerosol delivery. Preferably the particles may have diameters in the range of 0.005 to 10 μm.

The term receiving material is understood to be widely defined as a model material interacting with the aerosol, onto which or wherein particles of the aerosol are deposited, i.e. a fraction of the totally administered aerosol dose interacting with the receiving material. For example the cells can be cultured alone or co-cultured, single layer or in several layers, in suspension or as resembling a piece of a tissue wall.

The model material e.g., cells, may be cultured on one or on both sides of a permeable carrier, such as a membrane, preferably a polycarbonate membrane.

The terms "exposure target" is also used in the context of present invention and should be regarded to have the similar general meaning as "receiving material" namely target for the aerosol delivery with inventive system and methods.

The term model material is a model resembling an air-blood barrier in the respiratory tract.

The term model material may include any type of material that resembles the air-blood-barrier of the respiratory tract, preferably the pulmonary tract.

The receiving model material e.g. cells, is understood to be widely defined as cells interacting with the aerosol, onto which, or wherein particles of the aerosol are deposited, i.e. a fraction of the totally administered aerosol dose interacting with the deposited cells.

In the context of the present invention, a receiving material can be a model material consisting of isolated cells, cultured alone or co-cultured, in a single layer or several layers, or on both sides of the permeable carrier, in suspension and also as resembling a piece of a tissue wall.

In one general aspect, the present invention relates to a method of obtaining a controlled exposure of model material to an aerosol. The method comprises the steps of providing a container comprising the model material, inserting an exposure cap into said container so as to obtain a substantially sealed environment during the exposure, introducing a controlled aerosol flow to an upper part of the exposure cap and transporting the aerosol towards the surface of the model material with a flow rotating around a central axis of the exposure cap. The model material is so admitted to be contacted with the aerosol, while the model material container is shielded from contact with the aerosol. Aerosol that is not retained by the model material during the exposure procedure is transported away through an outlet function in the exposure cap in an axially upwards directed flow, separated from the downwards directed aerosol flow in the exposure cap. The outlet function can be provided with any conventional flow generating means in order to assist to generate a correct flow through the exposure cap. In one aspect, the aerosol is transported from the inlet with a flow rotating around a central axis of the exposure cap with a flow rate that has substantially decreased when the aerosol is exposed to the model material. In other terms the rotation around the central axis of the aerosol flow has ceased or substantially ceased. The flow rate can for example be arranged to gradually decrease when the aerosol travels towards the model material. The flow rate of the aerosol, when brought to contact with or introduced to the area of the model material, can be can be decreased to a preset value adapted to the model material or any other conditions of a test model.

In the method so described, the exposure cap is adapted to fit with the dimensions of the model material container retaining the model material in its bottom and extend to the region of its upper surface in order to accomplish a sealed environment during the aerosol exposure. In applications described in more detail below, the model material container is an essentially cylindrical container with cells cultured on a membrane in its bottom and the exposure cap is accordingly adapted. In one aspect, the described method comprises transporting the remaining aerosol from a single outlet in the lower part of the exposure cap with a single flow coinciding with the central axis of the model material container. In one aspect of the method, the aerosol is contacting the model material with an essentially constant flow shear rate along the surface of the model material, in order to obtain an even aerosol distribution of the model material. The method can also comprise a step of collecting remaining aerosol in exposure filters, i.e. aerosol not deposited to the model material. The method can also comprise detecting the concentration of aerosol introduced to the exposure cap. For these reasons, the method can further comprise estimating the deposited dose of the exposure from the detected aerosol concentration, filter deposited aerosol and a calculated aerosol deposition factor. In applications including viable cells in the model material these can be contacted with a perfusion fluid during an exposure with aerosol in order to resemble an airway-blood barrier condition. Accordingly with methods wherein the aerosol comprises a test substance, such as a drug candidate, the methods further comprise determining a mass balance of the remaining test substance rinsed from the model material container and test substance accumulated in the perfusion fluid, thereby determining the initially deposited dose of the exposure.

The described inventive method advantageously (1) minimizes or counteracts any losses of aerosol material to the equipment necessary for performing the exposure of the model material container such as the exposure cap and tubing, (2) provides means for exposing the surface of the model material as evenly as possible, and (3) restricts the exposure of the model container to the model material surface only. The method implies that the inserted exposure cap aligns to the model material in the container a suitable manner so substantially only the model material surface is exposed to the aerosol. For this reason, a correct estimate of the model-retained substance can be obtained even if the entire model container is rinsed in a suitable solvent after the exposure cap has been removed. Among many other advantages, the method particularly facilitates the correct determination of a mass-balance of an exposure and cycle and the establishment of highly reproducible exposure conditions.

The method is adaptable to different modes of introducing aerosol for exposure of the model material. In this context, the skilled artisan perceives that in many applications it is desirable to generate an even and controlled exposure throughout the surface of the model material fronting the introduced aerosol.

Many different ways of aerosol concentration detectors can be envisioned, such as aerosol particle detectors by optical means. With the method the model material can be subjected to a contacting perfusion fluid, subsequently collected by a fraction collection in order to closely determine the interactions between the model material and the aerosol, for instance how living cells in the model material metabolizes or biologically react to an agent comprised in the aerosol.

In one aspect, the present invention relates to an exposure cap for establishing a controlled and even exposure of a model material, which can resemble an air-blood barrier, to different test aerosols. The exposure cap generally is provided with an upper part adapted to receive an inlet flow of an aerosol; and a lower part, adapted to be aligned to the model material, to collect the aerosol stream following its exposure of the model material and to shield the model material container from the aerosol. The exposure cap thereby comprises an inlet duct with a tangentially located inlet orifice for receiving the aerosol in its upper part and for generating an aerosol flow from the upper part to the lower part which rotates around a central axis in order to contact the model material; and a single outlet duct for transporting remaining aerosol from the model material from the lower part to an outlet in the upper part. The outlet duct has an outlet orifice located at a defined height from the model material, and preferably the outlet duct is located along a central axis longitudinally extending between the lower and the upper part of the exposure device.

The rotating aerosol flow serve to provide an even aerosol concentration in the flow meeting the model material. This arrangement creates an even inlet stream of aerosol and an even or constant, controlled, flow shear flow can be accomplished around the entire perimeter of the model material. These conditions can be controlled by the aerosol inlet flow rate in the inlet duct, the diameter of the inlet orifice and the height between the model material and the outlet orifice. By modeling these parameters, the exposure cap can be adapted to different exposure models designed for special aerosols and model materials and yet obtain control over aerosol concentration and flow shear rate when the aerosol is introduced to the model material. For such purposes, the exposure cap is designed or operated to admit a rotating aerosol flow or an aerosol flow and the admitting the rotation to cease or substantially ceased before exposure to the model material, in order to counteract concentration gradients in the aerosol, while a funnel-shaped flow is generated from the model material surface to the outlet orifice of the outlet conduit. The design and operation of the exposure cap device thereby admits even and controlled exposure conditions between the aerosol and the model material.

In one aspect, the exposure cap comprises an inner, central body defining the inner wall of annular duct for transportation of aerosol from the tangential inlet orifice to the model material. The inner body has an extension that admits an annular slit in the lower part of the exposure cap for transportation of aerosol from the annular duct along the model material surface to the outlet duct. In this arrangement, the annular slit extends between the upper surface of the model material and the lower end of the inner body. Preferably, the lower part of the inner body comprises a funnel-shaped cavity extending from the peripheral lower end of the inner body to the outlet orifice of the inner duct, thereby defining a cavity height. In this embodiment, the cavity height and the slit height are adapted so the aerosol is transported with essentially constant flow shear rate along the surface of the model material. Preferably, the inlet orifice of the outlet duct has a diameter less than the width of the annular duct inner wall diameter. Preferably, the outlet duct is located essentially along a central axis longitudinally extending between the upper and lower parts. It is additionally preferred that the crossectional area of the annular duct is less than ¾ of the surface of the model material.

In one aspect, the device has an inner central body with a funnel-shaped extension in its lower part facing the model material, towards an inner wall of the exposure cap and admits that the annular duct has an essentially larger area in crossection than the annular slit. This arrangement contribute to admit a sufficient homogeneity of the aerosol by admitting a sufficient rotation of the aerosol before the aerosol flow transforms to a axially directed downwards flow towards the annular slit and the exposure area of the model material With the inventive exposure cap, an even flow shear field over a circular model surface can be accomplished by rotating the incoming aerosol from the inlet along the perimeter, then controlling the rotation volume by adjusting the height of the axial outlet above the center of the model surface. A suitable rotation and downward movement within the annulus can be controlled by 1) aerosol flow rate, 2) the cross-sectional area of the inlet duct mouth, and 3) the width of the annulus compared to the cavity height. The shape of the funnel-shaped cavity can be used to fine tune the rotating flow field over the model surface.

The exposure cap can be aligned to the model material resembling air blood-barrier in a manner that a substantially sealed environment is obtained during the exposure of aerosol. In this context aligned to means that it is sufficiently close to the model material and can, for example mean that the exposure cap can be releasably connected to a container including the model material. In one alternative, the exposure cap is of a cylindrical shape, it may also be a truncated cone. Other shapes are conceivable to be adapted to fit with specific culture containers. The outlet conduit of the exposure cap, preferably is connected to an exposure filter for collecting aerosol particle transported away from the model material. Further, the outlet conduit can be connected to a rotameter or mass flow regulator for controlling the flow rate. Further, the exposure cap suitably is made from a material that minimizes or counteracts adhesion of aerosols to its aerosol exposed surfaces, so unwanted deposition of particles is minimized on its inner surface. Suitable materials may be injection moulded plastics, such as Teflon.

The invention also relates to a system suitable for studying or predicting the interaction between a model material resembling the air-blood-barrier in the respiratory tract and an aerosol. The system comprises an exposure unit and an aerosol transporting unit that transports aerosol from an aerosol generating source to the exposure unit. The exposure unit comprising an exposure cap as described in previous sections above, a container comprising a model material which is adapted to receive the exposure cap so that the model material obtains a controlled exposure i.e. of the aerosol. The exposure unit further comprises a perfusion tray for establishing contact between a perfusion fluid and the model material in the container. A suitable arrangement for establishing contact between an aerosol exposed model material and a perfusion fluid is described WO 2008/153493. The aerosol transporting arrangement transports the aerosol from an aerosol generating source to the inlet orifice of an exposure cap. The aerosol transporting arrangement comprises an exposure flow line with one or more branches connected to one or more exposure caps transporting the aerosol from said exposure line to the aerosol inlet of the exposure cap. Advantageously, the outlet of the exposure flow line is provided with an end filter in order to obtain control of any aerosol not having been distributed to the exposure unit(s). The aerosol transporting arrangement is also sealingly connected to an aerosol generator which can be of the type disclosed in U.S. Pat. No. 6,003,512 which is suitable for producing high quality aerosols. The aerosol transporting arrangement can also include an aerosol particle detecting instrument to improve the control of what dose that reaches the exposure target of model material. The aerosol transporting arrangement further can comprise features disclosed in WO 2009/002267, such as an aerosol holding chamber of the vertically oriented conically shaped type described in this document. In the system, the perfusion tray is preferably connected to the container and it is provided with an inlet for perfusion fluid and an outlet for perfusion fluid. The inlet of the perfusion tray is preferably arranged so substantially the entire model material is evenly contacted with flowing perfusion liquid during and after an exposure cycle with aerosol. A suitable design of the perfusion tray is essentially circular in cross section, even if other configurations are fully conceivable, with an inlet and an outlet which are symmetrically located in a peripheral region of the tray. Preferably, the inlet and outlet are located in diametrically opposite directions between at least two parallel ridges, serving as flow directors or flow regulators for the perfusion fluid. In one aspect, the ridges a parallel and equidistant to the inlet and the outlet, respectively in order to admit a controlled, directed flow path along the membrane. For example two parallel ridges can extend in opposite directions from an essentially circular tray wall, while the ridges having the same angle against the inlet and outlet flow, respectively. In order to further control the perfusion conditions and a correct collection of perfusion fluid in fraction collectors or similarly auxiliary devices, the perfusion tray can be connected to a control device capable of controlling the fluid pressure against the membrane. For this purpose the control device can monitor and adjust the level of perfusion fluid in perfusion fluid container connected to the perfusion tray inlet. In the system, the perfusion tray, exposure cap and other parts of the system may be available as disposable units.

The following detailed description shows a number of examples of the inventive system and its operation which are not intended to limit the scope of protection as outlined by the appended claims.

SHORT DESCRIPTION OF DRAWINGS

Figure 4:
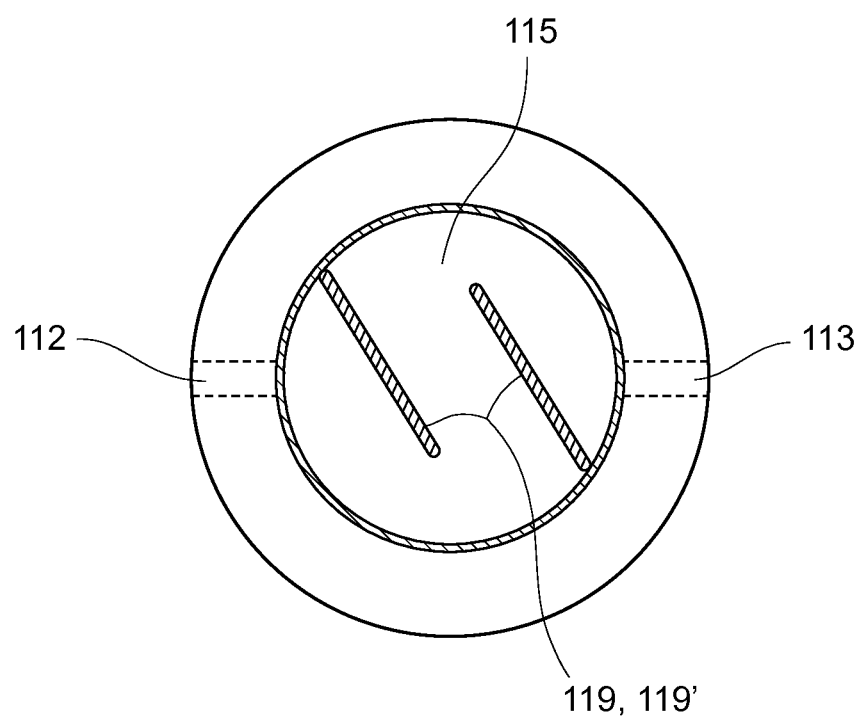

FIG. 4 schematically shows the perfusion tray.

DETAILED DESCRIPTION OF THE INVENTION

Before the invention is disclosed and described in detail, it is to be understood that this invention is not limited to particular compounds, configurations, method steps, substrates, and materials disclosed herein as such compounds, configurations, method steps, substrates, and materials may vary somewhat.

It is also to be understood that the terminology employed herein is used for the purpose of describing particular embodiments only and is not intended to be limiting since the scope of the present invention is limited only by the appended claims and equivalents thereof.

If nothing else is defined, any terms and scientific terminology used herein are intended to have the meanings commonly understood by those skilled in the art to which this invention pertains.

It must be noted that, as used in this specification and the appended claims, the singular forms "a", "an" and "the" include plural referents unless the context clearly dictates otherwise.

The term "about" as used in connection with a numerical value throughout the description and the claims denotes an interval of accuracy, familiar and acceptable to a person skilled in the art. Said interval is ±10%.

Other features and uses of the invention and their associated advantages will be evident to a person skilled in the art upon reading the description and the examples.

It is to be understood that this invention is not limited to the particular embodiments shown here. The following examples are provided for illustrative purposes and are not intended to limit the scope of the invention since the scope of the present invention is limited only by the appended claims and equivalents thereof.

Figure 1:
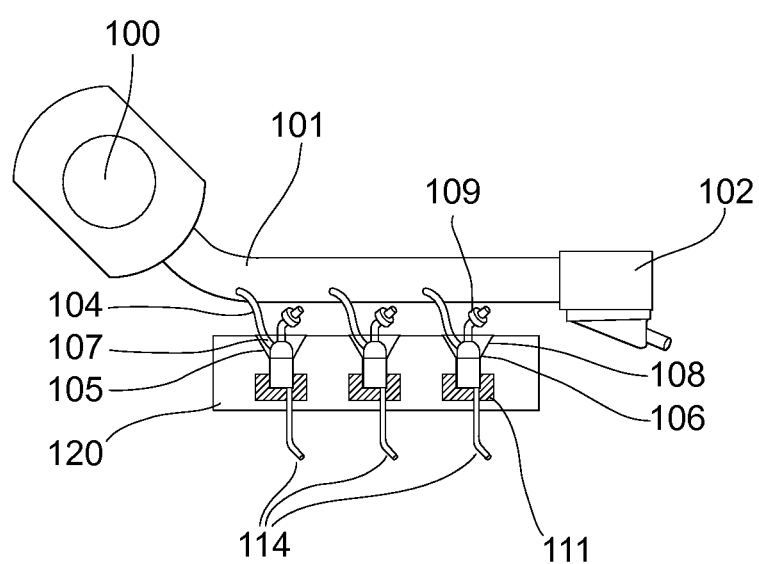
FIG. 1 shows a schematic drawing of a system for exposing cultured cells to an aerosol according to the present invention.

FIG. 1 shows a schematic drawing of a device for studying controlled exposure of a model material i.e. a cell layer, in vitro to a test aerosol.

The system comprise an aerosol generator (not shown) situated on the left side of a light beam instrument (100), an exposure flow line (101) connected to an end filter (102), the exposure flow line contains three branching points (104), each connecting an exposure unit (105), respectively, to the exposure flow line (101). The exposure unit (105) include an exposure cap (106) which comprises an inlet orifice conduit (107) and an outlet orifice conduit (108), an exposure filter (109) connected to a rotameter. The exposure cap (106) is in contact with a cell culture container, not shown (See FIG. 2), that is in turn in contact with a perfusion tray (111) (FIG. 3) comprising an outlet conduit orifice (113) that may be connected to a fraction collector (114) (FIG. 1). The temperature of the exposure unit is controlled by using a heating block (120), with one or several bores adapted to receive one or several exposure units, respectively. The heating block (120) is preferably made of steel. In FIG. 1, the device is shown with three exposure units (106), each comprising a commercial culture container with cultured cells.

When operating the system of FIG. 1, the aerosol is generated and passes from an aerosol generator (not shown) via a light beam instrument (100) coupled to an exposure flow line (101) that contains three dividing branching points (104) that each is connected to an inlet conduit (107) located in the upper parts of respective exposure cap (106). In each exposure cap, a flow of aerosol rotates downwards around a central axis of the cap is generated so that essentially only the layer of cells is evenly exposed to controlled amounts respirable aerosol at a time. Each cap has an outlet conduit (108) for transporting remaining aerosol from lower part through an opening in its upper part, where an exposure filter (109) collects all remaining aerosol. A rotameter (not shown) is connected to each outlet conduit (109) generating a constant flow rate through each branch of the exposure system. In addition, the overall flow rate of the exposure line is accomplished with yet another rotameter or similar device located downstream of the end filter (102). The cell culture container comprises a layer of cells cultured on one or both sides of a permeable membrane and which is contacted by a perfusate fluid which resembles the blood circulation in the airway mucosa on the other side of the permeable membrane. The flow rate of the perfusate fluid will be kept at a rate to resemble the flow rate in the mucosa. When chosen in the range of 0.4 ml/min for a model membrane 12 mm in diameter the renewal rate will be similar to that in the mucosa.

The thickness of the perfused layer below the permeable membrane (see FIG. 2, 115) will be approximately 0.5 mm, exemplified by 0.2 mm, in a way similar to the distribution of the rich superficial network of capillaries of the airway mucosa. The perfusate fluid will be transported in single-pass mode by the membrane and then immediately fractionated into suitable vessels e.g. a 96 well plate for analysis in a mass spec. A special fraction collector has been developed where the fraction sizes are not dependent on drop formation and are only controlled by the flow rate and the desired time window for the sample withdrawal. In this way, up to three wells may be exposed and samples withdrawn in parallel from one aerosol exposure. It is only the cell layer at the bottom of the well that shall be exposed with a good surface evenness and not in the inner walls of the test material container (Transwell® cup), which is the case with the Cultexsystem and similar systems. The aerosol will be slowly rotating downwards around the axially located aerosol outlet (108) in the upper part of the exposure cap, to be subsequently sucked out of the exposure unit via the aerosol outlet conduit (108) which is centered above the middle of the circular surface coated with cells.

Following exposures both the trans-epithelial absorption of dissolved substances and eventual biological reactions in the cells caused by the tested substances will be studied, as it will be manifested by the production and excretion different markers from the cells.

Figure 2:
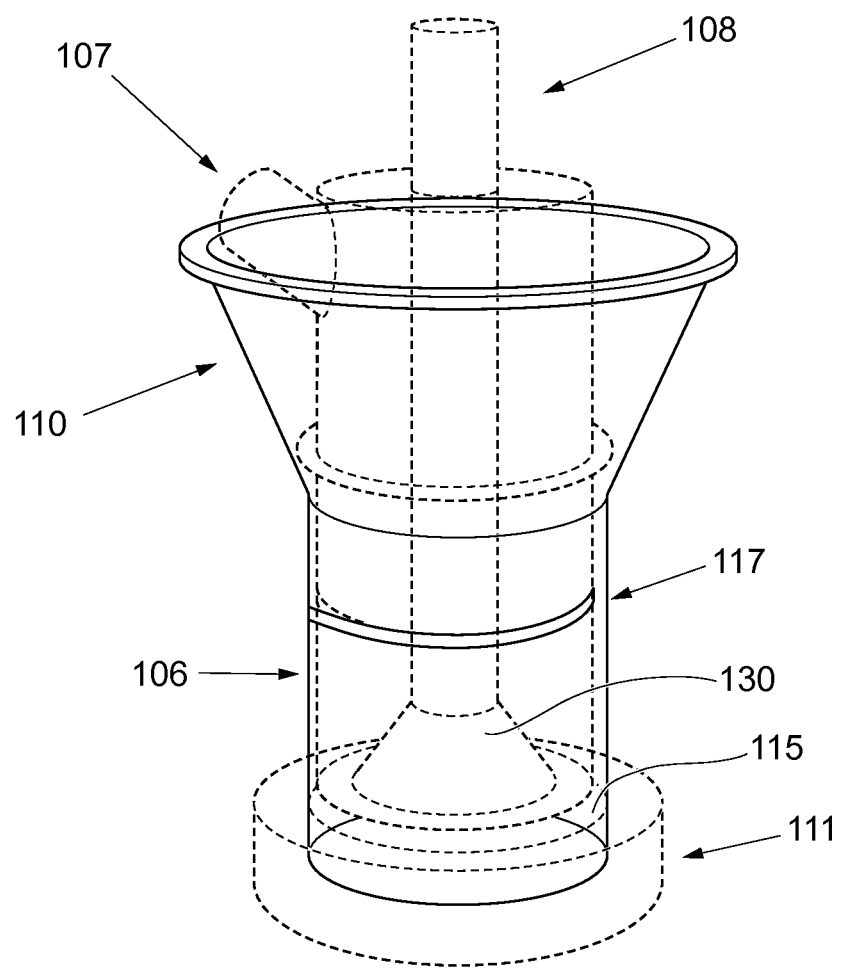
FIG. 2 shows schematic drawing of the exposure unit inserted in a conventional cell culture container, an exposure cap and a perfusion tray.

FIG. 2 shows a schematic drawing of an exposure unit (105) comprising a conventional cell culture container (Transwell® cup). The dotted lines show where the exposure cap (106) and the perfusion tray (111), respectively, are connected to assemble the exposure unit included in the system of FIG. 1. The exposure cap (106) of FIG. 2 has an inlet duct (107) with a tangentially locate inlet orifice. The exposure cap covers the inside of the Transwell cup down to the edge of the cell-covered membrane (115). This is to prevent any aerosol exposure outside of the cell-coated surface, and a correct figure for cell-retained aerosol material will be obtained even if the entire Transwell unit is rinsed in solvent after the exposure cap and tray have been removed. The cells are cultured on a permeable membrane located at the bottom of the Transwell® cup and are perfused by a thin layer of perfusate fluid that is pumped into the gap of the perfusate tray under the permeable membrane in a configuration chosen to resemble the blood circulation of the airway mucosa. FIG. 2 further shows the outlet conduit (108) centrally located in the exposure cap having an outlet orifice at a defined height above the model material, here represented by the cell covered membrane (115). In operation, an aerosol introduced through the tangential inlet orifice of the inlet conduit (107) and rotates downwards in the hollow exposure cap, between the inner wall and the centrally and symmetrically placed outlet conduit (108). The rotation speed is controlled by aerosol inlet flow rate, the diameter of the inlet orifice and the height between the outlet orifice and the model material. A flow with even flow shear rate and concentration of aerosol will now be distributed over the model material for the exposure and a funnel-shaped flow will generated in the direction of the outlet orifice.

Figure 3:
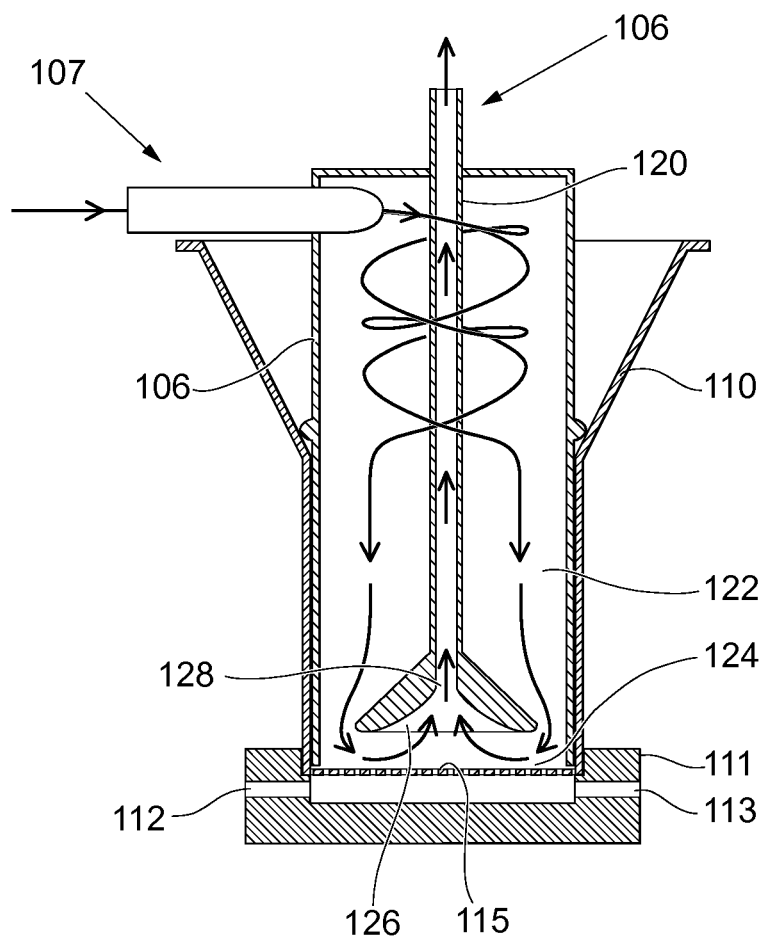
FIG. 3 shows an embodiment of exposure cap as inserted in cell culture container attached to a perfusion tray.

FIG. 3, shows a crossectional view of a special embodiment of an exposure cap (106) with an inner body (120). The exposure cap (106) is inserted in a cell culture container (100) having viable cells culture on the membrane (115). The exposure cap shields the cell container inner wall during the exposure in this inserted position in order to minimize and control aerosol transportation losses. The exposure cap (106) is provided with inlet conduit for aerosol (107) having a tangentially located inlet orifice and an axially extending outlet duct (108) arranged centrally and symmetrically in the inner body (120). An annular duct (122) is admitted between the inner body (120) and the inner wall of the exposure cap for downwards aerosol transportation. The inner body (120) axially extends towards model material represented by the cells of the membrane (115) to admit an annular slit (124). The lower part of the inner body (120) has funnel-shaped cavity or recess (126) extending from the periphery to the centrally located inlet orifice (128) of the outlet duct (108). The embodiment depicted in FIG. 3, shows how the annular body (122) extends in the funnel shaped extension 130 that extends towards an inner wall admits the annular slit (124). By the configuration of the funnel shaped extension and the dimensions annular duct (124) to be essentially narrower than the annular duct concentration gradients in the aerosol can be avoided or counteracted and a homogeneous exposure of aerosol can be established. By the so configured exposure cap, a controlled and extended downwards rotating flow can be established in the upper part of the exposure, before the aerosol is transported axially downwards towards the exposure area and the membrane (115).

In operation the arranged of FIG. 3, an aerosol is introduced with the tangentially located orifice of the inlet duct (107) so a downwards rotating aerosol flow is obtained in the annular duct (122) as described to the annular slit (124) and distributed along the cell culture for an aerosol exposing period. Remaining aerosol is transported away from the cell culture through the cavity (126) and into the outlet duct (108) which is connected to a conventional flow generating means (not shown). The so described embodiment admits even flow shear rate of aerosol along the surface of the model material, providing an even and controlled deposition of aerosol particles to the cultured cells and thereby realizing the many advantages of the invention outlined in earlier discussions.

FIG. 3 also shows the perfusion tray (111) attached to cell culture container (110) with the inserted perfusion cap (106). FIG. 4 schematically shows the perfusion tray (111) with diametrically opposite inlet and outlet (112, 113) and two intermediary ridges or baffles (119,119') serving as perfusion flow distributors. The perfusion tray for the provided with means for attachment and sealing to the cell culture container so a gap of about 0.2 mm is provided between the tray and the permeable membrane. As previously explained the perfusion tray can be accommodated in a heating block. In operation, the model material of the system (e.g. cells) is in contact with the perfusion fluid. A perfusion fluid is flowing through the perfusion tray, in order to stimulate the dissolution and absorption into the circulating blood of solutes emanating from the particles in the model material. The perfusion flow will receive the agent dissolved or metabolized, and diffused through the model material and membrane and be transported away for subsequent analysis. The perfusion fluid is generally adapted to interact with the model material in a manner that resembles the natural blood flow in the mucosa with a high renewal rate. Typically, this would correspond to a flow rate of on the order of 0.4 ml/min in a 12 mm diameter container. More specifically the perfusion fluid should be a physiologically acceptable fluid compatible with the model material. The perfusate pressure against the insert membrane can preferentially be regulated by adjusting the level of the perfusate outlet tube from the inserts as to achieve a suitable pressure head with a negative or positive static pressure component acing against the insert membrane. It is then important to prevent droplet formation at the tube exit, because the perfusate surface tension in the recurrent drops will cause an undulating pressure against the insert membrane.

The described system can advantageously be adapted to provide a controlled exposure simultaneously to a plurality of containers with model material, e.g. culture containers with cells. The containers can be of a conventional type with the model material, e.g. a cell culture on membrane. The exposure cap preferably is adapted to cover the entire inside of the container except the model material membrane during an aerosol exposure. Advantageously, in an exposure with a test substance, rinsing the model container with solvent after removal of the exposure cap will only recover model-retained substance. The system will provide highly reliable conditions by establishing similar or essentially identical exposure conditions in each container. In order to establish a reliable control system, wherein rotameters or mass flow regulators control and monitor the flow rate in the outlet conduits from the exposure caps and will thereby serve to control inlet flows from the branches of the exposure flow line so each model material (cell culture) obtains a similar exposure condition.

The inventive system is equally useful for estimating or predicting a deposited dose of an aerosol when the cell retained fraction of a substance cannot be measured, or for further pharmacokinetic modeling with isolated cells or another model material. Dummy containers with similar model material can then be used in line with the study containers to estimate the deposited dose of aerosol.

One advantage of an embodiment is the low amount of test compound needed, e.g. active substance in a pharmaceutical composition. For example, less than 1 mg test compound is enough to simultaneously expose three units each comprising a 12 mm well, respectively. Accordingly, the present invention admits improved methodology of screening drug candidates or other substances of interest.

Further the present invention of controlled exposure makes it possible to easily control the mass balance in the system; i.e. the deposited dose of aerosol is calculated as the sum of the remaining substance in the model material, e.g. cells and the cumulative amount in the perfusate. Because only the model material surface of the material container is exposed to the test aerosol, the correct fraction of material-retained substance can be obtained, even if the entire model container is rinsed in the analysis solvent.

Another advantage is that the model material is continuously provided with fresh media, i.e. perfusate fluid, where the used perfusate fluid containing absorbed or metabolized test substance from the aerosol particles are collected and analyzed.

A further advantage is that the aerosol may be evenly distributed into a plurality of culture containers, preferably three culture containers at the same time (SD+/−15%).

The interaction of the aerosol with the model material could be due to physical-chemical properties such as density of particle deposition, particle size, dissolution- and absorption rates, or biochemical properties such as metabolism or other effects.

In the context of the present invention, a deposited model material may be cultured cells, such as isolated primary cells, preferably isolated epithelial cells and possibly endothelial cells or other relevant cell types from the respiratory tract.

Suitable cells can be isolated primary cell, preferably isolated epithelial primary cells or COPD cells or cells isolated from a person suffering from asthma, it could also be a cell line, such as A 549 cells, preferably of epithelial origin and it could also be isolated stem cells, preferably stem cells that will differentiate into an epithelial cell type or any type of suitable cell. In one embodiment the cells are derived from the respiratory tract, more preferably isolated cells derived from pulmonary cells. In another embodiment the cells are co-cultured with another cell type, i.e., feeder cells.

The cell culture container may comprise one or several layers of cells on one or both sides of a model membrane, or cells cultured in a suspension.

The cells cultured may also be co-cultures, e.g. epithelial cells co-cultured with endothelial cells to resemble a wall of an organ with an inner part and outer part, respectively.

Advantageously, the system can be used when screening drug candidates based on their interaction properties with a model material resembling the air-blood-barrier. Firstly, a powdered dose of a drug candidate is aerosolized and the system is adapted to determine the predicted dose deposited in the material container (Mdep). Secondly, the predicted deposition of the powdered drug can now be used for running the system to expose a model material to the same aerosol for determining how the drug candidate interacts with the model material at the desired dose level. In other terms the determination of dose to be expected in the model material, admits that the system can be directly run with optimized exposure times and other operation conditions in subsequent tests with the model material when only low amounts of test material and few model material containers are available. The model material can be cells preferably human cells in a culture container/vessel. Preferably the transport aerosol flow is kept essentially at the same rate, wherein the flow is controlled by a rotameter or mass flow regulator. Preferably and advantageously, small amounts of drugs are used, in the mg range such as 0.1 to 3 mg.

By following these routines, the general advantages of the system in operating with optimized amounts of expensive material are further enhanced and quick, reliable discrimination between different drug candidates can effectively be performed at an early preclinical stage. Interaction studies made available with the method include not only absorption studies of the drug candidate, but is also equally feasible for studying a number of physiological effects including drug activity exerted in or via lung tissues, such as metabolism, pharmacological- and toxicological responses including onset of therapeutic action, as well as bioavailability and pharmacokinetic aspects. The presently invented system and the methodologies using the system will reduce and simplify the discovery and preclinical phases of drug development and thereby be of significant benefit to bring down the costs in an industry suffering from increasing burdens when attempting to find new original products for market approval. The system and the methods described are equally useful in diagnostic applications, wherein the described methodology can be applied of determining pulmonary deposition and determining airway sensitivity to an agent.

The same benefits will be evident for a diagnostic application regarding low dosing and test accuracy. The present invention in the form of the earlier disclosed methods, exposure cap and system is also intended to be applicable for biological validation of drug formulations with commercially available inhalators or nebulizers as aerosol generators. In such applications, the present invention admits a convenient and reliable evaluation of aerosolized drug formulations biological performance in terms of particle dissolution and pharmacokinetic characteristics, as well as the suitability of the available administration tools to sufficiently perform a controlled pulmonary administration of selected drug formulations.

We claim:

1. A method of obtaining a controlled exposure of a model material to an aerosol comprising the steps of;
   i. providing a container comprising the model material;
   ii. inserting an exposure cap into said container so as to obtain a substantially sealed environment during the exposure;
   iii. introducing a controlled aerosol flow to an upper part of the exposure cap and transporting the aerosol towards the surface of the model material with a flow rotating around a central axis of the exposure cap;
   iv. admitting the aerosol to contact the model material, while shielding the model material container from aerosol contact; and
   v. transporting remaining aerosol away from the model material surface in an axially upwards directed separate flow.

2. The method according to claim 1, comprising transporting the remaining aerosol from a single outlet in a lower part of the exposure cap with a single flow coinciding with the central axis of the model material container.

3. The method according to claim 1, comprising collecting remaining aerosol in exposure filters and detecting a concentration of aerosol introduced to the exposure cap.

4. The method according to claim 3, comprising estimating a deposited dose of the exposure from the detected aerosol concentration, aerosol deposited into the exposure filters and a calculated aerosol deposition factor.

5. The method according to claim 1, comprising contacting a model material resembling an airway-blood barrier with a perfusion fluid.

6. The method according to claim 5, wherein the aerosol comprises a test substance, wherein the method comprises determining a mass balance of a remaining test substance rinsed from the model material container and test substance accumulated in the perfusion fluid, thereby determining an initially deposited dose of the exposure.

7. The method according to claim 1, comprising admitting the aerosol contacting the model material with an essentially constant flow shear rate along the surface of the model material.

8. The method according to claim 1, wherein a flow rate of the aerosol decrease from the upper part of the exposure cap towards the surface of the model material, preferably by admitting a rotational flow around central axis in the upper part to transform to an axially downward flow towards the surface of the model material.

* * * * *